United States Patent [19]

Allcock et al.

[11] 4,278,660

[45] Jul. 14, 1981

[54] COMPLEX OR SALT OF A PLATINUM (II) COMPOUND AND A NITROGEN CONTAINING POLYMER

[75] Inventors: Harry R. Allcock, State College; Robert W. Allen, University Park; John P. O'Brien, State College, all of Pa.

[73] Assignee: Research Corporation, New York, N.Y.

[21] Appl. No.: 958,976

[22] Filed: Nov. 9, 1978

Related U.S. Application Data

[62] Division of Ser. No. 792,608, May 2, 1977, Pat. No. 4,151,185.

[51] Int. Cl.³ .................. A61K 31/74; A61K 31/555; A61K 31/28

[52] U.S. Cl. ...................................... 424/78; 424/245; 424/287

[58] Field of Search .................... 260/429 R; 424/287, 424/245, 78

[56] References Cited

U.S. PATENT DOCUMENTS

| | | | |
|---|---|---|---|
| 3,892,790 | 7/1975 | Tobe et al. | 260/429 R |
| 3,904,663 | 9/1975 | Tobe et al. | 260/429 R |

FOREIGN PATENT DOCUMENTS 1432562  4/1976  United Kingdom ..................... 424/287

OTHER PUBLICATIONS

American Druggist, p. 33, 1969.
Leh et al., J. of Pharmaceutical Sciences, 65(3), 315-328, (1976).
Meischen et al., J. Natl. Cancer Inst. 57(4), 841-845, (1976).
Belluco, Organometallic and Coordination Chemistry of Pt., Academic Press, N. Y. 547-548, (1974).

*Primary Examiner*—Jerome D. Goldberg
*Attorney, Agent, or Firm*—Dennis P. Clarke

[57] ABSTRACT

A cis- complex or -salt of a square planar platinum compound and a nitrogen containing oligomer or polymer prepared by reacting a platinum (II) compound with a nitrogen containing oligomer or polymer in an organic solvent or an acidic aqueous medium, said complex or salt being useful for treating animal malignant tumor cells sensitive to cis-square planar platinum compounds.

2 Claims, No Drawings

COMPLEX OR SALT OF A PLATINUM (II) COMPOUND AND A NITROGEN CONTAINING POLYMER

This is a division of application Ser. No. 792,608, filed May 2, 1977, now U.S. Pat. No. 4,151,185.

BACKGROUND OF THE INVENTION

Square planar platinum complexes such as cis-$(NH_3)_2Pt(II)Cl_2$ are known. Their widespread use as chemotherapeutic drugs, however, is limited by their rapid rate of excretion and the kidney damage which results from this effect. It has also been shown that the chemotherapeutic effects of these compounds are accompanied by such toxic side effects as bone marrow depletion and damage to the intestinal mucosa.

It is hypothesized that many of these side effects, particularly kidney damage, result from the fact that the platinum derivatives are small-molecule complexes that can be excreted rapidly through the semipermeable membranes of the kidney system.

It is an object of the invention to provide cis- platinum (II) complexes and salts which are effective anti-cancer agents but which do not exhibit toxic side effects such as kidney damage.

SUMMARY OF THE INVENTION

It has been discovered that forming complexes or salts of the square planar platinum compounds with nitrogen containing oligomers or polymers reduces to a considerable degree the toxic side effects of these platinum compounds. Due to the relatively large size of the oligomer or polymer molecules, the complexes or salts cannot be excreted through the semi-permeable membranes of the kidney, thereby considerably reducing the excretion rate of the platinum compound. Advantageously, the slow decomposition of the complex or salt under the influence of the hydrolytic system of the body provides a slow-controlled release of the platinum compound.

The present invention embodies cis- complexes or -salts of a square planar platinum compound and a nitrogen containing oligomer or polymer.

A further embodiment of the invention comprises a method for the preparation of the above-described complex by reacting the square planar platinum compound with a nitrogen containing oligomer or polymer in an organic solvent.

A further embodiment of the invention comprises a method for forming the above-described salt by reacting a square planar platinum compound with a nitrogen containing oligomer or polymer in an acidic aqueous medium.

A further embodiment of the invention comprises a composition and a method of treating animal malignant tumor cells sensitive to cis-square planar platinum compounds wherein the active ingredient is a cis- complex or -salt of a square planar platinum compound and a nitrogen containing oligomer or polymer.

DETAILED DESCRIPTION OF THE INVENTION

The invention is predicated on the discovery that complexation (or salt formation) of known platinum compounds with nitrogen containing polymers or oligomers renders the chemotherapeutic agents less toxic, particularly with respect to the kidneys, while not affecting the anti-cancer properties thereof.

Any square planar platinum compound capable of forming cis- Pt(II) complexes useful as chemotherapeutic agents may be employed according to the present invention. Preferred platinum compounds include the haloplatinates, particularly potassium tetrachloroplatinate, i.e., $K_2PtCl_4$. The latter compounds have been heretofore utilized for the preparation of various anti-cancer complexes. See Rosenberg et al, *Nature* (London), Vol. 222, page 385 (1969) and Connors et al, *Platinum Coordination Complexes in Cancer Chemotherapy*, Springer-Verlag Berlin, Heidelberg. New York (1974).

The haloplatinates are usually reacted with suitable reagents to form complexes of the general formula $R_2PtCl_2$ wherein R is a low molecular weight ligand such as $NH_3$ or an amine. These complexes comprise relatively small molecules which are rapidly excreted through the semi-permeable walls of the kidneys thereby resulting in a high degree of toxicity. Reaction of the haloplatinates with nitrogen containing polymers or oligomers results in comlexes and salts having a relatively large molecular size thereby preventing their rapid excretion through the kidney walls.

Any suitable nitrogen containing polymer or oligomer may be employed for formation of the complexes and salts in accordance with the present invention. Particularly preferred are the polyphosphazenes, particularly those having the structural formulae:

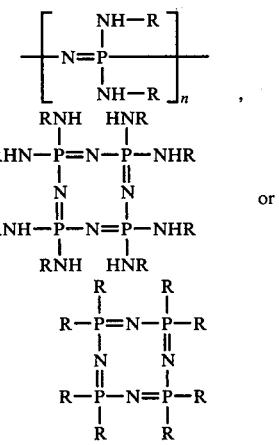

wherein: n represents the degree of polymerization, and R is alkyl, preferably lower alkyl, alkoxy, preferably lower alkoxy, aryloxy, halo, or an amino acid ester residue.

Other suitable nitrogen-containing polymers include polyvinyl pyridine and polyvinylpyrrolidone.

The degree of polymerization of the high polymer is not overly critical. Generally, polymers having a degree of polymerization such that n=1000 to about 20,000 are suitable.

The preferred polyphosphazenes are those wherein R is a low molecular weight aliphatic group such as lower alkyl, particularly methyl.

Suitable polyphosphazenes are described in H. R. Allcock, *Phosphorous-Nitrogen Compounds*, Academic Press, 1972; H. R. Allcock, Chem. Rev. Vol 72, page 315 (1972); H. R. Allcock et al, Inorg. Chem., Vol 11, page 2584 (1972); and H. R. Allcock, Science, Sept. 24, 1976, Vol. 193, page 1214.

The critical requirements for a suitable anti-cancer complex are that the polymer or oligomer be water-soluble, non-toxic and possess coordination sites for the binding of platinum, and that the ultimate complex contain two cis- ligand atoms, preferably chlorine.

The nature of the compound formed by the reaction of the nitrogen-containing polymer or oligomer with the platinum compound depends upon the reaction medium employed. Where the reaction is conducted in an organic solvent medium, the product is a neutral, square planar platinum complex. Where the reaction medium is an acidic aqueous medium, the end product is a tetrahaloplatinate salt.

REACTION IN ORGANIC MEDIA

Any suitable organic solvent medium may be employed for carrying out the reaction between the platinum compound and the nitrogen-containing polymer or oligomer. Preferred solvent media include acetone, methanol, chloroform, chlorobenzene, benzene, methylene chloride, diethyl ether, toluene, xylene, carbon tetrachloride, heptane, etc. It is only necessary that the organic medium be a suitable solvent for the reactants and that it have no deleterious effect on the reaction.

The following examples are illustrative of this aspect of the invention:

EXAMPLE 1

Synthesis of $[NP(NHCH_3)_2]_n$

Hexachlorocyclotriphosphazene, $(NPCl_2)_3$, was purified for polymerization by vacuum sublimation at 50°/0.1 torr, followed by recrystallization from hot n-heptane at a temperature below 75°. The first crop of crystals recovered at 25° was filtered off, dried in vacuum, and vacuum sublimed. A 150 g portion of this material was placed in a 32.5×3.5 cm constricted Pyrex tube. Air was removed on a vacuum line for 30 min. at 0.1 torr, and the contents were subjected to a melt-freeze-evacuate cycle before the tube was sealed. The tube was then encased in a wire screen jacket and was heated in a thermoregulated oven at 250° for 20 hours. The mixture of polymer and unchanged trimer was then subjected to vacuum sublimation at 50° to remove the trimer.

A viscous solution of the above poly(dichlorophosphazene) (80 g, 0.69 mol-monomer units) in tetrahydrofuran (1800 ml) was prepared. Methylamine (250 ml, 175 g, 5.52 moles) was condensed from a cylinder by means of a cold finger cooled in a Dry Ice-acetone mixture. The methylamine was dried over sodium spheres. It was then evaporated at 25° and recondensed into a flask which contained tetrahydrofuran (1500 ml) at 0°. The flask was swept with dry nitrogen. To this vigorously stirred solution was added the solution of poly(dichlorophosphazene) over a period of 2 hr. After the addition was complete, the reaction mixture was allowed to warm slowly to 25°, and stirring was continued at this temperature for 72 hr.

Solvent was then removed from the reaction mixture with the use of a rotary evaporator, and the residue was washed with n-heptane and dried in vacuum. Purification by dissolution of the product in water (1000 ml) and dialysis against water through Curtin 077-040 dialysis tubing for 72 hr. The solution was concentrated to 250 ml in a rotary evaporator, and the viscous polymer solution was cast on Teflon to yield thin films (30.7 g). These were dried in vacuum at 25° for 24 hr.

Reaction of $[NP(NHCH_3)_2]_n$ with $K_2PtCl_4$

A solution of the above-prepared $[NP(NHCH_3)_2]_n$ (2.08 g, 2×10$^{-2}$ mol) was prepared in chloroform (100 ml). Solution was complete after a period of 2 days at 25°. $K_2PtCl_4$ (0.83 g, 2×10$^{-3}$ mol) and 18 crown-6 ether (1.056 g, 4×10$^{-3}$ mol) were dissolved in chloroform (100 ml) during a period of 2 days. The two solutions were then mixed, diluted to 300 ml by the addition of chloroform, and allowed to stir at 25° for 14 days. After this time, a light yellow, amorphous precipitate (1.78 g) had formed, and this was removed by filtration. A sample of the product (1.25 g) in water (200 ml) was subjected to dialysis against water for 48 hr. at 25°. No evidence was seen for migration of the color. Both the undialyzed and dialyzed samples were prepared as thin films by solution casting on a Teflon support, followed by drying in vacuum at 25°. Anal. for the undialyzed polymer: C, 19.3; H, 7.2; N, 34.5; Cl, 4.5; P, 25.2; Pt (by difference), 9.3.

The product was found to conform to the structural formula:

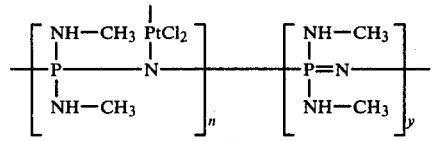

wherein n:y≃17:1

EXAMPLE 2

Synthesis of $[NP(NHCH_3)_2]_4$

Octakis(methylamino)cyclotetraphosphazene was prepared by the reaction of $(NPCl_2)_4$ with excess methylamine. The product (mp 200°) was recrystallized from ethanol.

Synthesis of cis-dichloro[octakis(methylamino)cyclotetraphosphazene-N,N''].platinum(II), $Cl_2[N_4P_4(NHCH_3)_8]Pt(II)$ A solution of $K_2PtCl_4$ (0.83 g, 2×10$^{-3}$ mol) and 18-crown-6 ether (0.96 g, 3.64×10$^{-3}$ mol) in chloroform (100 ml) was prepared. The cyclic phosphazene, $[NP(NHCH_3)_2]_4$, (0.84 g, 2×10$^{-3}$ mol) was dissolved in chloroform (100 ml). Both solutions were stirred for 24 hr. to achieve complete solution and were then mixed. The resultant solution was boiled at reflux for 36 hr. in an apparatus protected from the atmosphere by a $CaCl_2$ drying tube, and was then allowed to stand at 25° for 2 weeks. The initial crop of yellow crystals (0.22 g) was removed by filtration. The filtrate was evaporated to dryness and the residue was extracted with ether (100 ml). The remaining residue was dried in vacuum and then dissolved in acetone (125 ml). This solution was heated at reflux for 24 hr., cooled to 25°, and filtered. After 3 days at 25° the filtrate yielded a crop of fine yellow crystals (0.16 g), mp 198°-200° (decomp). Anal. Calcd. for $C_8H_{32}Cl_2N_{12}P_4Pt$: C, 14.00; H, 4.67; N, 24.49; Cl, 10.34; P, 18.05; Pt, 28.45. Found: C, 14.04; H, 4.89; N, 24.60; Cl, 10.14; P, 17.92; Pt (by difference) 28.71.

The product was found to have the structural formula:

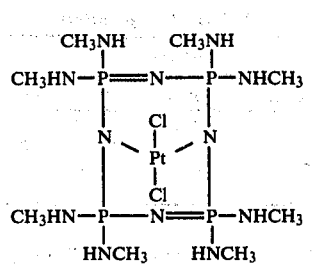

EXAMPLE 3

The compund, [NP(CH$_3$)$_2$]$_4$ (mp 160°-161° C., lit. 163°-164° C.) was prepared by the conversion of tetramethylphosphine disulfide to dimethyltrichlorophosphorane, and reaction of the latter with ammonium chloride (or ammonia) according to the process described by Allcock et al, Inorg. Chem., Vol. 16, p. 197 (1977).

Reaction with K$_2$PtCl$_4$

A solution was prepared of K$_2$PtCl$_4$ (0.42 g, 1.0×10$^{-3}$ mol) and 18-crown-6 ether (0.54 g, 2.0×10$^{-3}$ mol) in chloroform (25 ml). Octamethylcyclotetraphosphazene (0.30 g, 1×10$^{-3}$ mol) was dissolved in acetone (25 ml). The two solutions were mixed and allowed to stir at 25° for 5 days. Removal of the solvents in vacuum during 24 hr. yielded a solid conglometate. This was extracted with several portions of ether to remove any residual crown ether and collected over sintered glass using suction filtration. The crude material (0.62 g) was dried and then stirred in 50 ml of benzene. The solution was centrifuged to remove undissolved material and the mother liquor was decanted and dried at 25° in air for 24 hr. and in vacuo at 25° for an additional 4 hr. A crop of pale orange crystals was collected (0.20 g) mp 150-153 d.

The compound was found to have the structural formula:

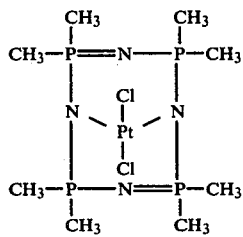

REACTION WITH PtCl$_2$

Octamethylcyclotetraphosphazene (0.50 g, 1.7×10$^{-3}$ mol) was dissolved in benzene (125 ml) and 25 ml of solvent were removed by distillation to remove traces of water as an azeotrope. Platinum dichloride (0.44 g, 1.7×10$^{-3}$ mol) was then added and the resultant suspension was heated at reflux for 72 hr. The solvent was removed in vacuo and the residue was subjected to sublimation at 100°/0.05 torr for 10 hr. White crystals of the starting phosphazene (0.12 g) collected on the cold finger. The non-volatile residue was then stirred as a suspension in acetone (100 ml) for 2 hr. and the mixture was filtered to yield 0.35 g of an insoluble solid and a brown-orange filtrate. n-Heptane (75 ml) was added to the filtrate, and slow evaporation of the solvents yielded a precipitate (0.089 g) of a red-brown product. This was washed with n-heptane and dried; mp 210°-212° (decomp). Anal. Calcd. for C$_8$H$_{24}$Cl$_2$N$_4$P$_4$Pt: C, 16.97; H, 4.26; N, 9.89; Cl, 12.52; P, 21.88; Pt, 34.45. Found: C, 17.10; H, 4.41; N, 9.79; Cl, 12.35; P, 21.79; Pt (by difference) 34.56.

With respect to the structural formula of the products described in Examples 2 and 3, it is to be understood that all P-N bonds attached to dicoordinate nitrogen atoms are resonance hybrids with the same bond length. P-N Bonds attached to tri-coordinate nitrogen atoms are longer, with no double bond characteristics.

REACTION IN AQUEOUS MEDIA

As noted above, reaction of the nitrogen containing polymers with the square planar platinum compounds in acidic aqueous results in the formation of tetrahaloplatinate salts. Any suitable acid may be employed for acidifying the aqueous medium. Hydrochloric acid is preferred. Generally it is preferred that the acidic solution be 0.1 to about 1.0 M with respect to acid. The following examples illustrate this aspect of the invention.

EXAMPLE 4

Reaction of K$_2$PtCl$_4$ with [NP(NHCH$_3$)$_2$]$_4$

A solution of K$_2$PtCl$_4$ (0.42 g, 1.0×10$^{-3}$ mol) in 0.1 molar aqueous hydrochloric acid (25 ml) was prepared. To this was slowly added, with stirring, a solution of [NP(NHCH$_3$)$_2$]$_4$ (0.42 g, 1.0×10$^{-3}$ mol) in 25 ml of 0.1 molar hydrochloric acid. After 1 hr. the reaction mixture was cooled to 0°. The light red crystals were filtered off, washed with methanol, and dried (0.65 g). A portion of the product (0.3 g) was recrystallized from 25 ml of boiling 0.1 molar hydrochloric acid. A solution of this material, H$_2$[NP(NHCH$_3$)$_2$]$_4$, in dimethylsulfoxide gave an ultraviolet-visible spectrum very similar to that of K$_2$PtCl$_4$ in the same solvent (absorption maximum at 333 nm). Anal. calcd. for C$_8$H$_{34}$N$_{12}$·P$_4$Pt: C, 12.66; H, 4.51; N, 22.14; Cl, 18.68; P, 16.32; Pt, 25.70. Found: C, 12.60; H, 4.48; N, 21.24; Cl, 18.21; P, 16.65; Pt (by difference) 26.82.

Neither the ultraviolet-visible spectrum nor the microanalytical data changed during recrystallization from boiling 0.1 molar hydrochloric acid. The structure of the compound was found to be:

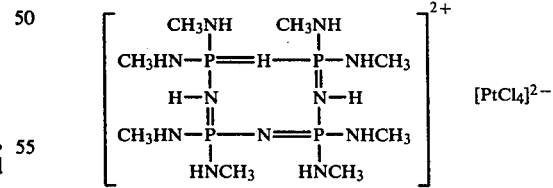

EXAMPLE 5

Reaction of K$_2$PtCl$_4$ With [NP(CH$_3$)$_2$]$_4$

A solution was prepared of K$_2$PtCl$_4$ (0.42 g, 1×10$^{-3}$ mol) in 0.1 molar hydrochloric acid (25 ml), and this was mixed with a solution of [NP(CH$_3$)$_2$]$_4$ (0.30 g, 1×10$^{-3}$ mol) in 0.1 molar hydrochloric acid (25 ml). An immediate, light red precipitate formed. The precipitate was filtered off, washed several times with acetone-water mixtures, and then dried in vacuum. Anal.

Calcd. for $C_8H_{26}N_4Cl_4P_4Pt$: C, 15.04; H, 4.07; N, 8.77; Cl, 22.20; P, 30.97; Pt, 18.95. Found: C, 15.04; H, 4.24; N, 9.02; Cl, 22.15; P, 30.54; Pt (by difference) 19.01.

The spectro and microanalytical results for this complex are consistent with the structural formula:

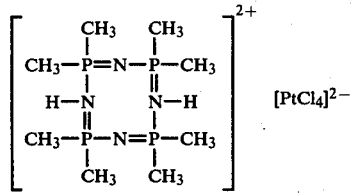

The complexes and salts were tested by the mouse P388 lymphocytic leukemia survival time test and by the Ehrlich Ascites Tumor Regression Test. All of the complexes and salts of the above examples were found to be effective agents. It is particularly noteworthy that the charged species or salts are effective agents since it was previously theorized that only neutral platinum complexes were effective agents.

In the Ehrlich Ascites Screen, $10^6$ cells were implanted I.P. into $CF_1$ male mice (30 g) on day zero. Test compounds were homogenized in 0.05% tween-80-$H_2$) to obtain a fine suspension and injected I.P at 0.5 mg/day (16.6 mg/kg). On the eighth day, mice were sacrificed and the total volume of ascites tumor fluid and a packed cell volume (ascrit) were determined in order to calculate the percent inhibition of tumor growth according to the method of C. Piantadosi et al, Sci., Vol. 58, p. 821 (1969). The results are set forth in Table 1.

TABLE 1

| Compound | No. of Mice | No. Mice Surviving after 8th Day | Ascrit | Vol. | % Inhibition |
|---|---|---|---|---|---|
| Ex. 1 | 7 | 5/7 | 35.6 | 0.54 | 86.4 |
| Ex. 2 | 7 | 5/7 | 36.0 | 1.52 | 61.3 |
| Ex. 4 | 7 | 6/7 | 29.6 | 1.06 | 77.8 |

TABLE 1-continued

| Compound | No. of Mice | No. Mice Surviving after 8th Day | Ascrit | Vol. | % Inhibition |
|---|---|---|---|---|---|
| Ex. 5 | 7 | 7/7 | 29.5 | 0.41 | 91.4 |
| Ex. 3 | 7 | 4/7 | 19.3 | 1.00 | 86.3 |
| 0.05% tween 80 | 7 | 7/7 | 40.0 | 3.53 | — |

The complexes of the invention may be admixed with any suitable carrier or adjuvant, such as isotonic saline, etc., and administered IP. Generally, dosages below about 20 mg/kg may be administered.

This invention arose from a project conducted in part with the support of the U.S. Army Research Office (G1124).

It is also to be understood that the platinum modified nitrogen-containing polymers possess other utilities. Thus, the platinum complex acts as a cross-linking agent for the nitrogen-containing polymer, thereby modifying its properties and providing for different applications thereof. For example, the platinum cross-linked polymers have a decreased water solubility, a high degree of coloration and are much stiffer than the non-crosslinked product.

What is claimed is:

1. A method of treating animal malignant tumor cells sensitive to cis-square planar platinum compounds in animals which comprises parenterally administering to an animal afflicted with said tumor cells a solution containing a complex or salt of the said cis-square planar platinum compound with a nitrogen container oligomer or polymer selected from the group consisting of polyphosphazenes, polyvinylpyridine and polyvinylpyrrolidone in an amount sufficient to cause regression of the animal tumor cells.

2. An anti-tumor composition in unit dosage form effective for treating animal malignant tumor cells sensitive to cis-square planar platinum compounds in animals containing an anti-tumor effective amount of a complex or salt of said cis-square planar platinum compound and a nitrogen containing oligomer or polymer selected from the group consisting of polyphosphazenes, polyvinylpyridine and polyvinylpyrrolidone and a pharmaceutically acceptable carrier therefor.

* * * * *